(12) United States Patent
Kay

(10) Patent No.: US 8,566,275 B2
(45) Date of Patent: *Oct. 22, 2013

(54) SYSTEMS AND METHODS FOR PROCESSING MEDICAL DATA FOR EMPLOYMENT DETERMINATIONS

(75) Inventor: Lay K. Kay, Pasadena, CA (US)

(73) Assignee: QTC Management, Inc., Diamond Bar, CA (US)

(*) Notice: Subject to any disclaimer, the term of this patent is extended or adjusted under 35 U.S.C. 154(b) by 124 days.

This patent is subject to a terminal disclaimer.

(21) Appl. No.: 12/884,118

(22) Filed: Sep. 16, 2010

(65) Prior Publication Data

US 2011/0106848 A1    May 5, 2011

Related U.S. Application Data

(63) Continuation of application No. 11/335,255, filed on Jan. 19, 2006, now Pat. No. 7,818,339.

(51) Int. Cl.
*G06F 7/00* (2006.01)
*G06F 17/00* (2006.01)
*G06Q 50/00* (2012.01)

(52) U.S. Cl.
USPC ............................ 707/603; 707/941; 705/3

(58) Field of Classification Search
USPC .......... 707/600, 603, 941; 705/2–4, 320, 321
See application file for complete search history.

(56) References Cited

U.S. PATENT DOCUMENTS

| | | | | |
|---|---|---|---|---|
| 5,367,675 A * | 11/1994 | Cheng et al. | ............................ | 1/1 |
| 6,049,794 A * | 4/2000 | Jacobs et al. | ..................... | 706/45 |
| 6,434,531 B1 * | 8/2002 | Lancelot et al. | ................... | 705/3 |
| 6,544,172 B2 * | 4/2003 | Toeppen-Sprigg | ........... | 600/300 |
| 6,604,080 B1 * | 8/2003 | Kern | ................................. | 705/4 |
| 6,865,581 B1 * | 3/2005 | Cloninger et al. | ................ | 705/9 |
| 6,988,088 B1 * | 1/2006 | Miikkulainen et al. | ......... | 706/14 |
| 7,260,480 B1 * | 8/2007 | Brown et al. | ................... | 702/19 |
| 7,698,154 B2 * | 4/2010 | Marchosky | ....................... | 705/3 |
| 2001/0041992 A1 * | 11/2001 | Lewis et al. | ....................... | 705/3 |
| 2001/0044735 A1 * | 11/2001 | Colburn et al. | .................... | 705/4 |
| 2002/0022975 A1 * | 2/2002 | Blasingame et al. | ............ | 705/3 |
| 2002/0035486 A1 * | 3/2002 | Huyn et al. | ....................... | 705/3 |
| 2002/0046199 A1 * | 4/2002 | Scarborough et al. | .......... | 706/21 |
| 2002/0069089 A1 * | 6/2002 | Larkin et al. | ...................... | 705/4 |
| 2002/0119433 A1 * | 8/2002 | Callender | ...................... | 434/322 |
| 2002/0138306 A1 * | 9/2002 | Sabovich | .......................... | 705/3 |
| 2003/0200123 A1 * | 10/2003 | Burge et al. | ....................... | 705/4 |
| 2004/0122707 A1 * | 6/2004 | Sabol et al. | ....................... | 705/2 |
| 2005/0033773 A1 * | 2/2005 | Roberge et al. | ............ | 707/104.1 |
| 2005/0256744 A1 * | 11/2005 | Rohde et al. | ...................... | 705/2 |
| 2007/0299674 A1 * | 12/2007 | Timko et al. | ...................... | 705/1 |

* cited by examiner

*Primary Examiner* — Jeffrey A Burke

(74) *Attorney, Agent, or Firm* — James W. Hill; Nathan S. Smith; McDermott Will & Emery LLP

(57) ABSTRACT

Methods and systems are described for automated processing of medical information for employment determinations. Based on an employment screening procedure for an applicant, medical information queries are automatically generated to provide instructions to medical providers for conducting physical exams and laboratory tests and for retrieving medical records. After medical information is collected according to the queries, the medical information and related requirements codes are displayed to program administrative personnel in a user-friendly format to assist in making an employment determination.

26 Claims, 5 Drawing Sheets

SYSTEMS AND METHODS FOR PROCESSING MEDICAL DATA FOR EMPLOYMENT DETERMINATIONS

REFERENCE TO RELATED APPLICATIONS

The present application is a continuation of and claims benefit of priority under 35 U.S.C. §120 from U.S. Pat. No. 7,818,339 application Ser. No. 11/335,255, filed Jan. 19, 2006, which is hereby incorporated herein by reference in its entirety.

BACKGROUND OF THE INVENTION

1. Field of the Invention

The present invention relates to automated systems and methods for processing medical data to support employment determinations.

2. Description of the Related Art

Corporations, government agencies, and other employers often require the gathering and evaluation of medical information to support employment determinations. For example, such employers may require employment screening procedures, periodic employment evaluations, evaluations of an employee's or potential employee's fitness for particular tasks, combination of the same and the like. Typically, such screening procedures (or "screenings") revolve around a triggering event, such as, an application for work, a certain period of employment, a set date on which employees are tested, an event that occurs with respect to the employee's workplace (e.g., a spike in radioactivity at a power plant), the results of a primary test (e.g., an employee or a relative discovers that he or she has cancer) and the like.

In order to evaluate the medical suitability of an applicant during a particular screening process, certain medical information is typically required. Medical information requirements are typically established by the employer responsible for the determination and are used by the employer to generate a specific suitability evaluation based upon the interpretation of that medical evidence. The requirements are specified by rules developed by the corporation, government agency or other employer, pertinent case law, government regulations, legislation and administrative decisions, and so forth. For example, the requirements may specify that if an applicant is applying for a particular form of employment, a medical provider must conduct certain physical examinations and laboratory tests on the applicant or ask certain questions. Requirements can also be specified by conventional medical knowledge, such as, for example, requiring a certain test to confirm a particular condition.

The requirements may be documented in a variety of formats, such as in manuals, databases, or other media. The collection of corporate rules, administrative decisions, pertinent legislation and case law governing employment is herein referred to as a "rules collection" governing employment. The rules collection typically specifies a capability, or lack of restriction, for the applicant to be acceptable to undertake or continue in a particular form of employment. It may, or may not, delineate a particular medical procedure that should be used to gather medical information needed for the determination.

In an evaluation process, the applicant typically visits a hospital, clinic or medical office. A medical provider such as a physician or a nurse collects medical evidence from the applicant to support an employment determination. The employment determination is typically made by personnel employed by the corporation, government agency or other employer based on the medical information collected by the medical provider and based on the rules collection. These personnel, referred to hereinafter as program administrative personnel, often support the employer in an administrative capacity and are often human resources personnel.

The medical providers often are not familiar with the rules collection relevant to the employment determination and may not collect the correct information, or may collect insufficient information, for making the determination. Therefore, the required medical information can be omitted and/or entered incorrectly, thus preventing a fast, accurate employment determination. In addition, the program administrative personnel, who typically have only limited medical knowledge, must spend considerable time reviewing the medical information collected by the medical providers.

SUMMARY OF THE INVENTION

In view of the foregoing, what is desired is an automated system that provides instructions to medical providers to collect medical information based on the rules collection for the employment determination. Furthermore, a system is needed that provides supporting information in a user-friendly format to assist program administrative personnel in making an employment-related decision based on collected medical evidence.

According to one embodiment of the present invention, a computer-implemented method of assisting medical information collection for an employment determination is disclosed. At least one screening procedure for assisting in the employment determination is identified, wherein the screening procedure is correlated, by a computer, with an employment event concerning an applicant. A plurality of medical information queries is automatically generated, the medical information queries being based on the at least one screening procedure and based on an employment rules collection. The plurality of medical information queries is stored in a first memory, and a plurality of medical information items concerning the employee is received into a second memory, the plurality of medical information items representing respective responses to the plurality of medical information queries.

According to another embodiment of the present invention, a computer-implemented method for facilitating an employment determination is disclosed. Medical information concerning an applicant may be received. An employment assessment based on the medical information may be automatically generated, wherein the medical information is obtained by a method comprising the following steps. At least one screening procedure is identified, wherein the screening procedure is triggered by an employment event. A plurality of medical information queries is automatically generated based on the at least one screening procedure and based on a rules collection. Answers to the generated medical information queries are received from an electronic data storage, said answers corresponding to the medical information.

According to another embodiment of the present invention, a computerized employment determination system is shown. The employment determination system comprises a rules mapping component adapted to map an employment rules collection into at least a first plurality of general medical information queries. The system further comprises a knowledge library adapted to store at least the first plurality of general medical information queries in a storage device. The system further comprises an applicant-specific query creation component adapted to create a selection automatically from the first plurality of general queries of a second plurality of applicant-specific medical information queries, the selection being based on at least one screening procedure. A protocol creation component is adapted to create automatically at least one data collection protocol based on the second plurality of queries.

According to another embodiment of the present invention, an automated system for assisting medical information collection for an employment determination is disclosed. An identification component that identifies at least one screening procedure for assisting in the employment determination comprises a part of the automated system, wherein the screening procedure is correlated with an employment event concerning an employee. The automated system further comprises a query generating component that generates a plurality of medical information queries, the medical information queries being based on the at least one screening procedure and based on an employment rules collection, and a storage component that stores the plurality of medical information queries. The system further comprises an intake component that receives into a computer storage medical information data concerning the employee, the medical information data representing respective responses to at least a portion of the plurality of medical information queries.

In other embodiments, an automated system for processing medical information for an employment determination is disclosed. The automated system comprises a mapping module, a library module, a query generation module and a protocol module. The mapping module is configured to map an employment rules collection into a plurality of general medical information queries. The library module is configured to store the plurality of general medical information queries. The query generation module is configured to receive screening procedure data and to generate, based at least in part on the screening procedure data, a plurality of applicant-specific medical information queries from a subset of the plurality of general medical information queries. The protocol module is configured to create automatically at least one data collection protocol based on the plurality of applicant-specific medical information queries.

In other embodiments, a machine loadable software program is disclosed for assisting medical information collection for an employment determination of an individual. The software program comprises: first computer instructions for mapping an employment rules collection into a plurality of general medical information queries; second computer instructions for receiving screening procedure data; third computer instructions for generating, based at least in part on the screening procedure data, a plurality of applicant-specific medical information queries from a subset of the plurality of general medical information queries; fourth computer instructions for creating at least one data collection protocol based on the plurality of applicant-specific medical information queries; fifth computer instructions for receiving medical information data indicative of respective responses to the applicant-specific medical information queries; and sixth computer instructions for outputting data indicative of an employment assessment based on the received medical information data.

For purposes of summarizing the invention, certain aspects, advantages and novel features of the invention have been described herein. Of course, it is to be understood that not necessarily all such aspects, advantages or features will be embodied in any particular embodiment of the invention.

DETAILED DESCRIPTION OF THE PREFERRED EMBODIMENTS

Embodiments of the present invention now will be described more fully hereinafter with reference to the drawings summarized above. The drawings, associated descriptions, and specific implementation are provided to illustrate embodiments of the invention and not to limit the scope of the disclosure.

Overview of Employment Determination System

Figure 1:
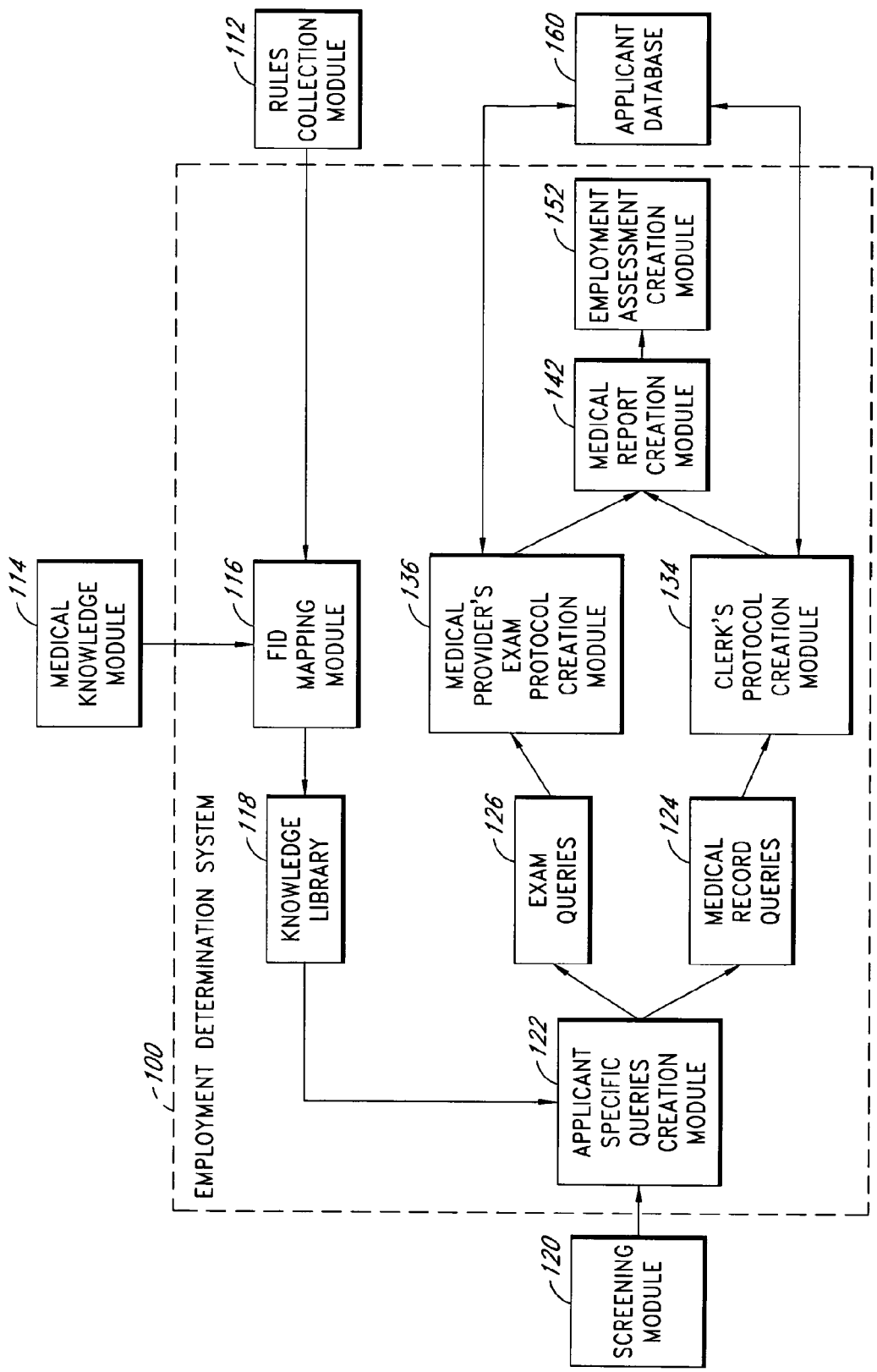
FIG. 1 illustrates a block diagram of an employment determination system, according to certain embodiments of the invention.

FIG. 1 illustrates a block diagram of an employment determination system 100, according to certain embodiments of the invention. In certain embodiments, the employment determination system 100 assists an employer and/or program administrative personnel in making an employment-related decision based at least on collected medical evidence. As illustrated, the employment determination system 100 receives input from a rules collection module 112, a medical knowledge module 114 and a screening module 120 and accesses data in an applicant database 160.

In certain embodiments, the employment determination system 100 communicates with one or more of rules collection module 112, the medical knowledge module 114, the screening module 120 and the applicant database 160 through a wired or wireless network, such as the Internet or an intranet. In certain embodiments, such communications may be through one or more of the following: dedicated communication lines, telephone networks, wireless data transmission systems, two-way cable systems, customized computer networks, interactive kiosk networks, automatic teller machine networks, interactive television networks and the like.

It will also be appreciated that at least one of the rules collection module 112, the medical knowledge module 114 and the screening module 120 may receive data input by one or more individuals. That is, in certain embodiments, one or more of these modules may receive data instead of or in addition to storing data electronically. Furthermore, in certain embodiments, at least one of the rules collection module 112, the medical knowledge module 114, the screening module 120 and the applicant database 160 may be integrated into the employment determination system 100.

With continued reference to FIG. 1, the rules collection module 112 and pertinent medical knowledge module 114 are organized by a FID mapping module 116 into a knowledge library 118. In certain embodiments, the rules collection module 112 may be constructed from general history and physical examination information requirements, occupation-specific requirements (e.g., a hearing conservation examination, lead exposure examination, liver toxic exam and the like), and applicant modifiers, such as, sex, race, smoker, and the like. Based on the screening procedure data from the screening module 120 and based on the rules collection or medical knowledge stored in the knowledge library 118, an applicant-specific query creation module 122 creates applicant-specific medical information queries. As used herein, the term, screening procedure, refers to some action by the employer to evaluate an applicant or employee based at least in part on medical information.

In certain embodiments, the applicant-specific queries are then separated into medical record queries 124 and exam queries 126 for physical exams and laboratory tests. The medical record queries 124 for medical records may be used by the clerk's protocol creation module 134 to create a clerk's data collection protocol to collect the required data from medical records. Alternatively, the medical record queries 124 may trigger an electronic records querying module (not shown) that facilitates the collection of the required data from electronic medical records (EMR) stored in the applicant database 160.

In certain embodiments, the exam queries 126 may be used by a medical provider's exam protocol creation module 136 to create a medical provider's data collection protocol to assist a physician, nurse or technician in reviewing and extracting data from charts, radiological study results, nuclear medicine laboratory results, present medication, allergy and chronic condition lists (e.g., from medical alert bracelets) and other medical records of the applicant. The exam protocol creation module 136 may also create a medical provider's data collection protocol to assist the medical provider in conducting histories of the present illness, past medical histories, family and social histories, a review of systems, physical exams, laboratory tests, interviews with friends and family of the applicant, and/or interviews of the applicant's prior medical providers. The provider's exam protocol creation module 136 may also use the exam queries 126 to create a questionnaire to be answered by the applicant.

In certain embodiments, a medical report creation module 142 uses the medical information collected from exams, tests, reviews, histories, interviews, applicant questionnaires and/or medical records to create a medical report. The employment assessment creation module 152 creates an employment assessment to assist program administrative personnel in making an employment determination. The collected medical information can also be stored in an applicant database 160.

Organizing Rules Collection into Knowledge Library

Still referring to FIG. 1, the rules collection module 112 stores and or receives the rules collection for employment screening, typically embodied in employment policy statements, legislation, administrative decisions and/or case law. The rules collection is preferably arranged in a hierarchy of information requirements. Occupation-specific required examination information, such as, for example, coal miner lung exam, pilot eye exam, lead exposure exam, liver toxicity exam, may be required in the specific instance wherein that occupational requirement is called for. Personal factor modifier requirements (e.g., sex, race, smoker) may be required when the applicant meets a personal modifier profile. The medical knowledge module 114 represents pertinent medical knowledge, such as instructions to a physician, lab technician or nurse for performing a physical exam or laboratory test. The rules collection and medical knowledge are organized by a FID mapping module 116 into field identification numbers (FIDs) and stored in a knowledge library module 118.

It will be understood that at least a portion of the rules collection and/or the medical knowledge may not be embodied in an electronic format. For example, the rules collection and/or medical knowledge may be recorded in one or more texts and/or documents. In such embodiments, one or more individuals may input the rules collection and/or medical knowledge into or through the rules collection module 112 and/or the medical knowledge module 114. Medical knowledge may also include the knowledge of one or more individuals.

In a preferred embodiment, data that may be required by the rules collection for making an employment assessment is identified by a FID. Examples of FID data fields include an "applicant name" field, a "heart rate" field, a "pulmonary capacity" field, and so forth. Each general medical information query is identified by a FID. A general medical information query corresponds to a medical information requirement specified by the rules collection or by medical knowledge. An applicant-specific medical information query is generated from at least a subset of the general medical information queries and is advantageously based on the applicant's occupation-specific examination requirements. Applicant-specific queries are further described in the subsection titled "Generating applicant-specific medical information queries."

In a preferred arrangement, each FID includes a category code, a requirements code and a data query code, separated by the underline symbol "_". For example, a FID can take the form of "H047_SM500_T001." The category code "H047" associates the FID with a category of queries concerning the eyes. The requirements code "SM500" associates the FID with a particular rule for determining whether a pilot meets the eyesight standards. The data query code "T001" associates the FID with a data query "Does the applicant have a corrected vision of 20/20 or better?" In certain embodiments, a query text table preferably stores the data query codes and the query text for each of the data query codes. The table may also store instruction text for each data query code as an instruction or explanation. The stored query text and instruction text can be later displayed in a medical provider's exam protocol, history or interview protocol, applicant questionnaire, clerk's data collection protocol, and/or medical report.

In one embodiment, a FID can take alternative forms. For example, in a relational database arrangement, a requirements code table can store the requirements code for each data query code, and a category code table can store the category code for each data query code. Therefore a FID need only include a data query code, and the requirements code and category code for the FID can be identified by referencing the requirements code table and the category code table. In an object-oriented arrangement, a FID can be an object that includes a data query object field, a requirements code object field and a category code object field.

Arrangement of Classes and Sub-Classes, Categories and Sub-Categories

Figure 2:
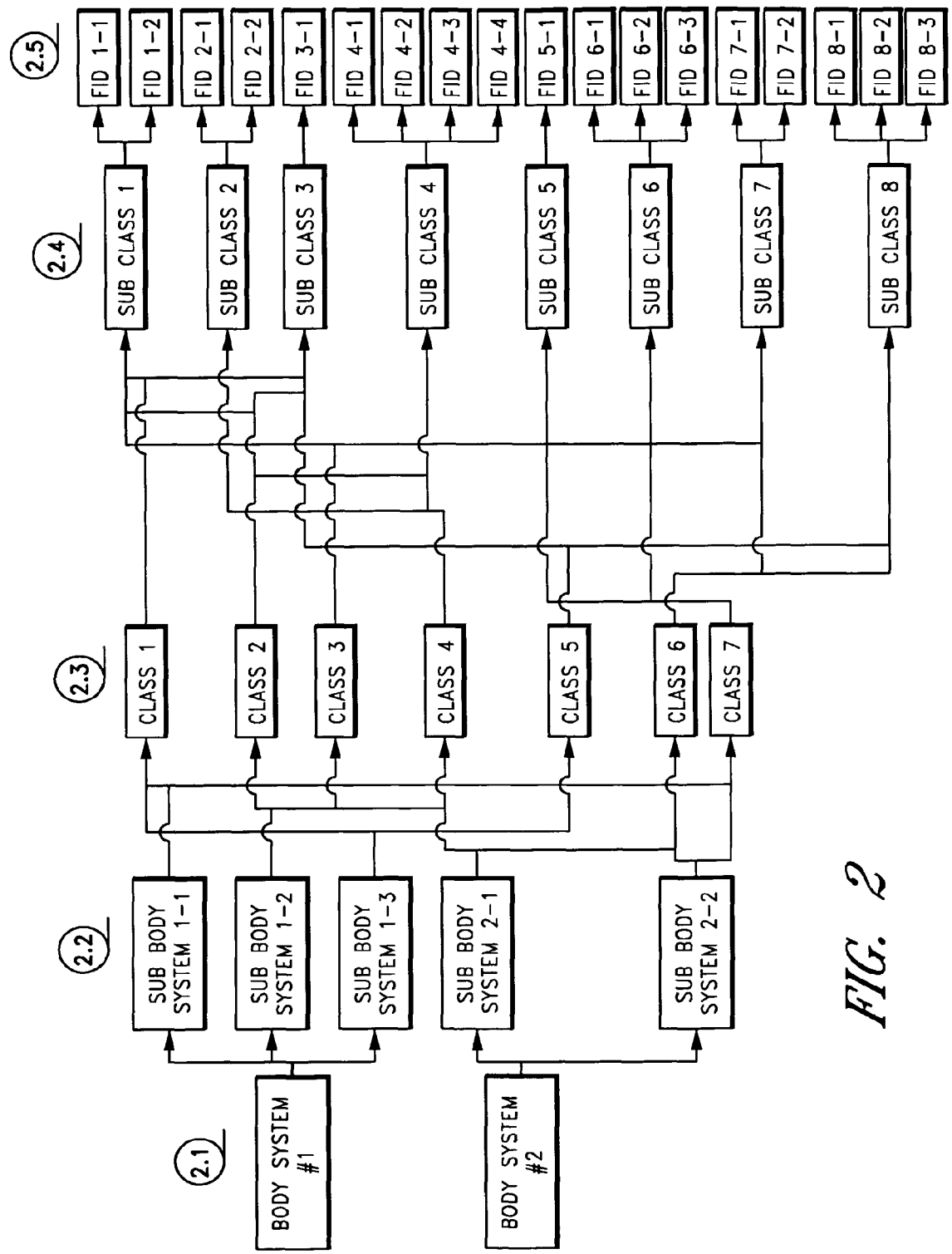
FIG. 2 illustrates an exemplary embodiment of a classification system for FIDs usable by the employment determination system of FIG. 1.

FIG. 2 illustrates an exemplary embodiment of a classification system for FIDs usable by the employment determination system 100. In certain embodiments, the employment determination system 100 classifies medical requirements into body systems 2.1. Body systems 2.1 may include the cardiovascular system, the respiratory system, infectious diseases, and so forth. In certain embodiments, the employment determination system 100 may classify a body system into one or more sub-body systems 2.2. For example, a "cardiovascular disease system" may include sub-body systems 2.2 such as myocardial-infarction sub-body system, arrhythmia sub-body system, and so forth. In certain embodiments, the sub-body system 2.2 is unique to one body system 2.1 and is not shared by multiple body systems 2.1.

As shown in FIG. 2, each sub-body system 2.2 is mapped to one or more classes 2.3. A class 2.3 represents a function within the sub-body system 2.2. For example, the lung sub-body system 2.2 can be mapped to a "history of smoking" class, a "history of general health" class, a "physical examination of the lungs" class, and so forth. In certain embodiments, sub-body systems 2.2 can share common classes. In certain embodiments, classes 2.3 are assigned priority numbers that identify a priority order among the classes 2.3.

Each class 2.3 can include one or more sub-classes 2.4. For example, a "vital signs" sub-class 2.4 can include data about the height, weight, pulse, and blood pressure of the applicant. Classes 2.3 may also share common sub-classes. For example, the "vital signs" sub-class 2.4 can be shared by multiple classes 2.3 because vital signs information is needed for the diagnosis of several different diseases and conditions. In certain embodiments, sub-classes 2.4 are assigned priority numbers that identify a priority order among the sub-classes 2.4.

As illustrated, a sub-class 2.4 includes one or more FIDs 2.5. For example, the "vital signs" sub-class may include a "height" FID 2.5, a "weight" FID 2.5, a "pulse" FID 2.5 and a "blood pressure" FID 2.5. In a preferred embodiment, each FID 2.5 belongs to only one sub-class 2.4. In one arrangement, each FID 2.5 includes a sub-class code that identifies the sub-class of the FID 2.5. In another embodiment, a sub-class table in the knowledge library 118 stores the FIDs 2.5 for each sub-class.

In other embodiments, classes and sub-classes are not introduced. For example, each requirements code and its general medical information queries may directly correspond to a collection of FIDs. The FID collections for two requirements codes may share one or more FIDs.

Figure 3:
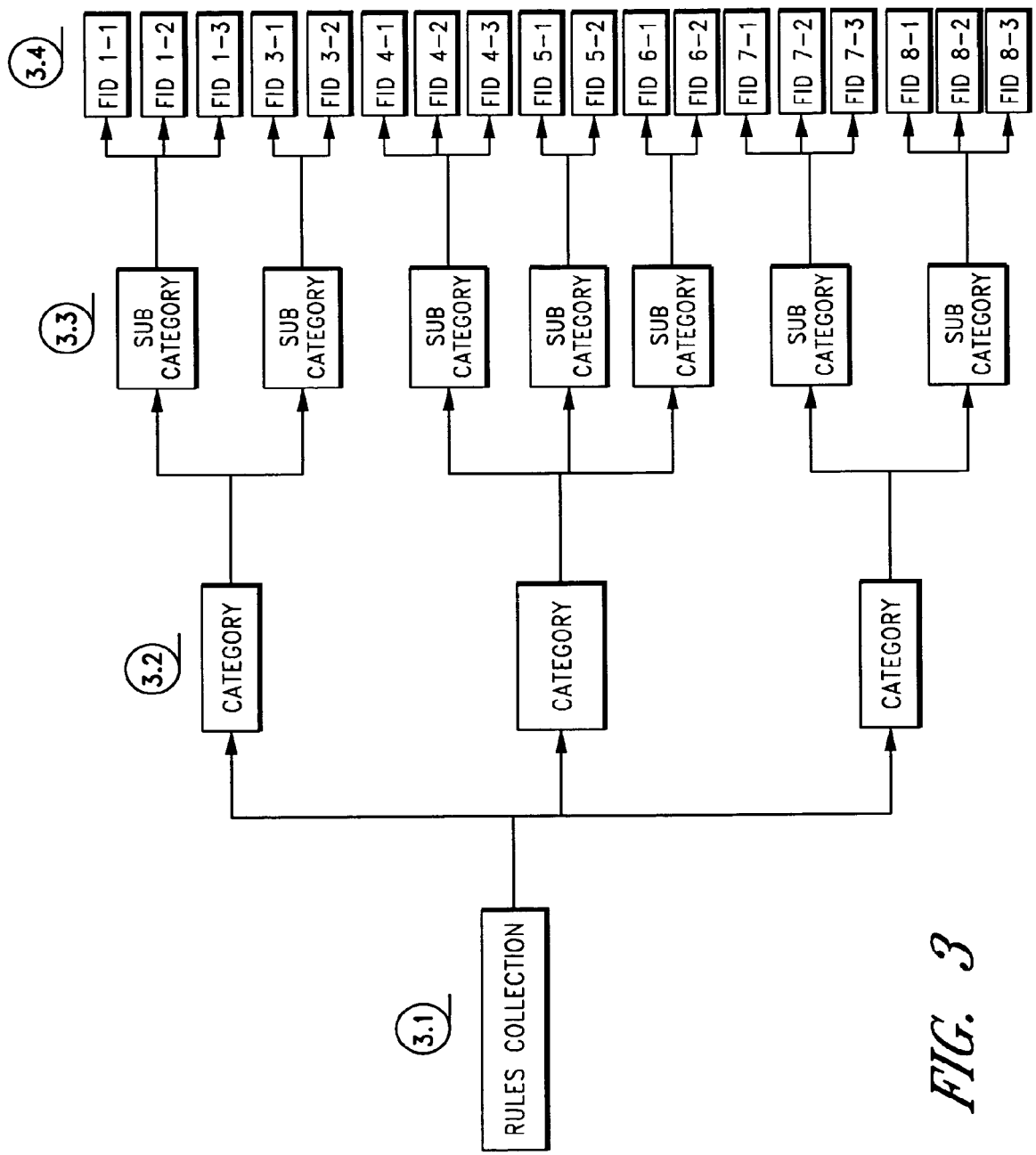
FIG. 3 illustrates an exemplary embodiment of an arrangement of data elements that make up a rules collection usable by the employment determination system of FIG. 1.

Referring to FIG. 3, data elements that make up the rules collection 3.1 are grouped by category 3.2 and sub-category 3.3. The categories 3.2 and sub-categories 3.3 preferably relate to classifications used by the employer. For example, categories 3.2 can include "General," "Complications," "Function," "Symptoms," "Tests," and so forth. A category 3.2 can be further classified into one or more sub-categories 3.3. For example, the "Function" category 3.2 may include the sub-categories 3.3 "ability" and "restriction." The "Tests" category 3.2 may include sub-categories 3.3 "confirmation," "essential," "indication," and "results." As shown, a sub-category 3.3 may include one or more FIDs 3.4.

Figure 4:
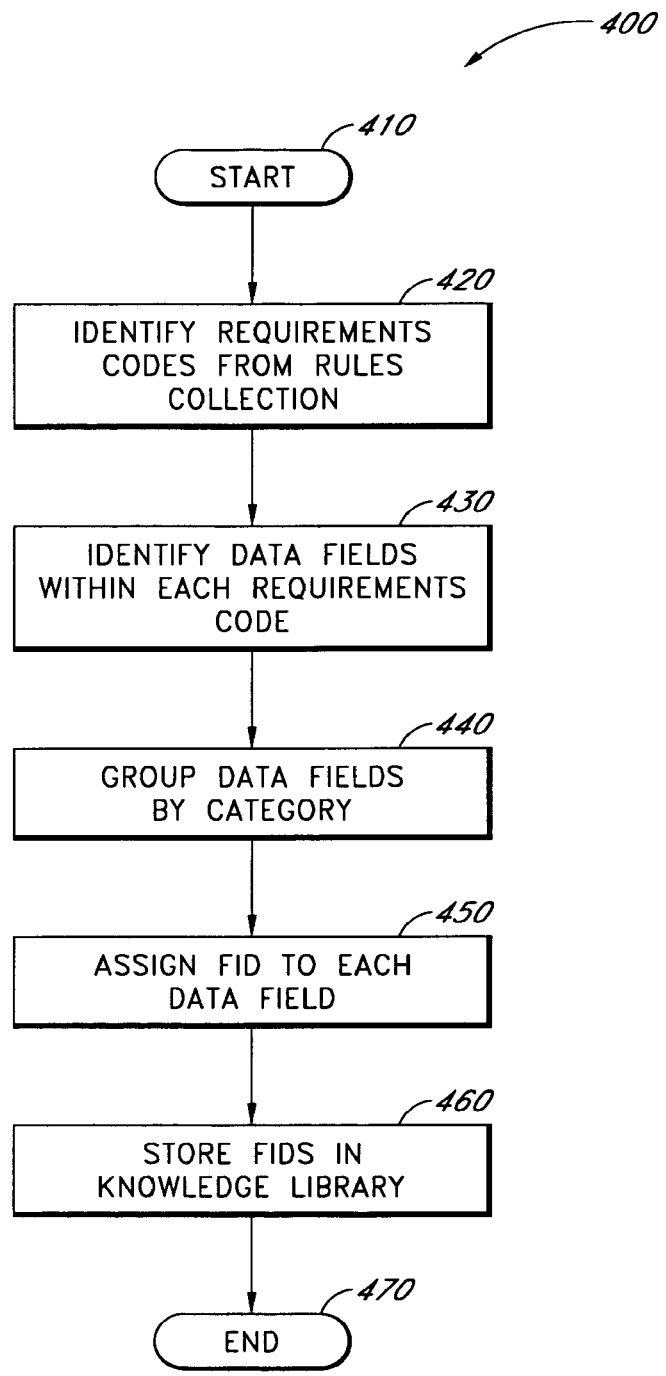
FIG. 4 illustrates an exemplary embodiment of an FID mapping process for organizing a rules collection usable by the employment determination system of FIG. 1.

FIG. 4 illustrates one embodiment of a FID mapping process 400 for organizing a rules collection into FIDs. For example, in certain embodiments, at least a portion of the process 400 may be performed by the FID mapping module 116 of the employment determination system 100. From a start Block 410, the process 400 proceeds to a Block 420 to identify requirements codes from one or more employers. The process 400 then proceeds to a Block 430 to identify data fields within each requirements code. Each data field represents a general medical information query. Data fields may also be identified based on pertinent medical knowledge, such as, for example, the knowledge of a experienced physician that certain medical information is needed to make an employment assessment.

The process 400 then proceeds to a Block 440 to group the data fields by category. In other embodiments, the data fields are further grouped by sub-category. The process 400 proceeds to a Block 450, where a FID is assigned to each data field. In a preferred embodiment, a category code, a requirements code and a data query code are advantageously assigned to each FID. In certain embodiments, the category code represents the category the data field is grouped into, the requirements code represents the requirements code for the data field, and the data query code represents the data query for the medical information query. The process 400 then proceeds to a Block 460 to store the FIDs in the knowledge library 118. The process 400 terminates at an end Block 470.

Generating Applicant-Specific Medical Information Queries

In FIG. 1, the applicant-specific query creation module 122 receives data from the screening module 120 and creates applicant-specific medical information queries based on the screening process data, characteristics of the applicant and/or by referring to the general medical information queries stored in the knowledge library 118. As would be well-understood by those of skill in the art, the screening module 120 may be related to employment screening procedures, periodic employment evaluations, evaluation of an employee's or potential employee's fitness for particular tasks, combinations of the same and the like. In certain embodiments, the screening and accompanying employment determination revolves around one or more triggering events, such as, an application for work, a certain period of employment, a set date on which employees are tested, an event that occurs with respect to the employee's workplace (e.g., a spike in radioactivity at a power plant), the results of a primary test (e.g., an employee or a relative discovers that he or she has cancer), or the like FIG. 5 illustrates one embodiment of a query-creation process 500 by which the screening type is used to generate queries.

Figure 5:
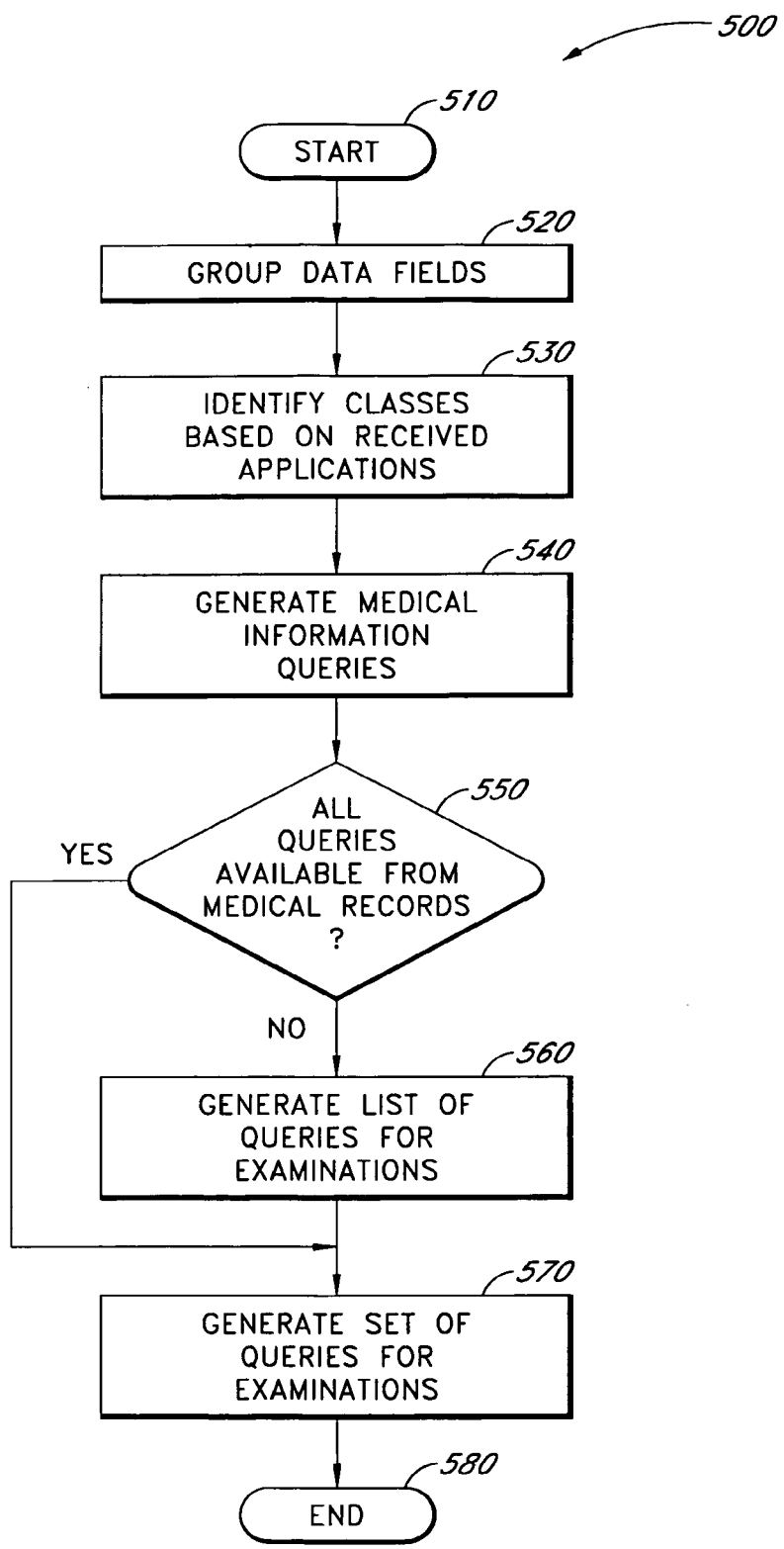
FIG. 5 illustrates an exemplary embodiment of a query creation process usable by the employment determination system of FIG. 1 for generating applicant-specific medical evidence queries.

Referring to FIG. 5, the process 500 starts from a start Block 510 and proceeds to a Block 520, where the query creation module 122 receives one or more screening requests from the screening module 120. In one embodiment, the query creation module 122 also receives other information provided by the applicant, such as the applicant's name, age or gender filled out by the applicant on a data entry form.

In preferred embodiments, the applicant may advantageously provide certain medical information in the form of a preliminary applicant questionnaire. This medical information may then be used by the applicant-specific medical information query creation module 122 to generate medical information queries.

Referring to FIG. 5, at Block 530, the query creation module 122 identifies the related classes based on the received screening data. In certain embodiments, the query creation module 122 may also identify one or more of the following: general information and physical examination requirements, specific screening data (e.g., a coal miner periodic evaluation), and personal factor modifier data. For example, if a received answer is "heavy smoker," the query creation module 122 may identify a "physical exam" class and a "pulmonary exam" class.

The relationships of medical conditions and related classes are stored in the knowledge library 118. The query creation module 122 also identifies sub-classes of the identified classes. In certain preferred embodiments, if two of the identified classes share common sub-classes, the duplicate sub-classes with the lower priority numbers are removed. From all the FIDs that belong to the identified classes, the duplicate FIDs can also be removed. In other embodiments, instead of identifying the related classes based on the received applications, the query creation module 122 identifies the related sub-classes, the related categories, or the related sub-categories. In another embodiment, the query creation module 122 directly identifies the related FIDs stored in the knowledge library 118 based on the received screening data.

At Block 540 of FIG. 5, the query creation module 122 selects those FIDs in the knowledge library 118 that belong to the identified classes and sub-classes. The selected FIDs form a set of the applicant-specific medical information queries. The set can be stored in a variety of formats, such as, for example, as a text string with FIDs separated by field delimiters such as colons or semicolons, as a text file with a FID in each line, as a table with each FID as a record, as a series of objects with each FID having a "next FID" pointer that points to the next FID object, and the like. This set of queries is preferably stored in a computer-readable storage, such as hard disk storage, solid state RAM, etc, and this data storage may be implemented using any type of computer storage device or devices, and using any type or types of data repositories (e.g., relational databases, files, caches, combinations of the same and the like).

In an embodiment, the query creation module 122 compares the information already received from the applicant and fills the related FIDs with such information. For example, if the applicant has provided his or her name, age and gender, the query creation module 122 then fills the related FIDs with the applicant-provided information. The details of filling a FID with collected medical information are described below in more detail.

From the Block 540, the process 500 proceeds to Block 550, where the query creation module 122 determines which of the generated applicant-specific queries may be satisfied from medical records. In another embodiment, a human operator reviews the generated queries and determines which of the queries may be satisfied from medical records. In still another embodiment, the query creation module 122 accesses an applicant's EMR or employer records and determines which generated applicant-specific queries may be thereby satisfied. In other embodiments, instead of determining on a per FID basis, the determination can also be made on a per class, per sub-class, per category or per sub-category basis.

If all generated queries may be obtained from medical and employment records, electronic or paper-based, then the process 500 proceeds to Block 570, and then the process 400 terminates at an end Block 580. Otherwise the process 500 proceeds to a Block 560, where the query creation module 122 generates a set of applicant-specific queries to be satisfied from physical exams, histories and/or interviews, applicant questionnaires, laboratory tests, and/or other medical provider input. At the Block 570, the query creation module 122 generates a set of queries whose results can be obtained from existing medical records. The applicant-specific queries generated at the Block 540 are thus separated into two sets of queries. In another embodiment, the queries generated at the Block 540 are separated into three sets: one set of queries to be satisfied from physical exams, histories, interviews and applicant questionnaires, another set to be satisfied from laboratory tests, and a third set to be satisfied from medical records.

Referring back to Blocks 530 and 540 of FIG. 5, when the applicant triggers multiple screenings, it is possible that some of the classes are identified more than once. The query creation module 122 searches for duplicate classes and eliminates such duplications. In other embodiments, the query creation module 122 can also search for and eliminate duplications on the sub-class or FID level.

In certain embodiments, each class is associated with a priority number stored in the knowledge library 118. In the case where multiple classes are called that examine the same sub-body system, the duplicate classes with the lower priority numbers are eliminated. In another embodiment, each FID is associated with a priority number stored in the knowledge library 118.

In an embodiment, the generated queries can be updated by a human operator. For example, a medical provider or program administrative personnel may review the generated applicant-specific queries and add, modify or delete one or more queries. This allows some flexibility and human control in the system 100. The human operator can also change the order of generated applicant-specific queries determined by the priority numbers.

The query creation module 122 may also check special rules stored in the knowledge library 118 for exceptions and updates. For example, exceptions and updates may be caused by changes in legislation, case law, and the employer's regulations. When the generated applicant-specific queries include a FID associated with a special rule, the special rule is retrieved from the knowledge library 118 and applied to include a special rule instruction with the FID, or to add, modify or remove other applicant-specific queries. The special rule can also change the order of generated applicant-specific queries determined by the priority numbers.

Creating Medical Provider's and Clerk's Data Collection Protocols

Referring back to FIG. 1, based on the generated set of applicant-specific queries for exams, the medical provider's protocol creation module 136 may create a medical provider's data collection protocol (also referred to as a physician's exam protocol). The provider's protocol creation module 136 may also create an applicant questionnaire based on the applicant-specific queries. Based on the generated set of applicant-specific queries for medical records, the clerk's protocol creation module 134 may create a clerk's data collection protocol. The generated set of applicant-specific queries may also trigger an electronic records querying module (not shown) that facilitates the collection of the required data from EMR or employment records.

The medical provider may advantageously use the exam protocol to examine the applicant and to preferably enter collected medical information into the protocol. In one embodiment, the exam protocol is displayed to the medical provider on the screen of an electronic device, such as a computer or a personal digital assistant, and the medical provider enters the collected medical information corresponding to each query into the electronic device. In another embodiment, the exam protocol is displayed to the medical provider in a paper report, and the medical provider enters the collected medical information on the paper report for a clerk to enter into a computer system.

The medical information collected by the medical provider is then stored in the employment determination system 100, preferably in computer storage, as discussed above. In certain embodiments, for each generated applicant-specific query and its FID, the corresponding medical information is simply inserted into the end of the FID. For example, for the FID "H047_SM500_T001" described above, if the medical provider determines that the pilot does have 20/20 vision, then the FID becomes "H047_SM500_T001_Yes," with the last field within the FID storing the value of the medical information. In another embodiment, a table includes an "original FID" field that stores the FID of each query and a "data value" that stores the medical information value of the corresponding FID.

To replace or to supplement the physician's exam protocol, the provider's exam protocol creation module 136 may create an applicant questionnaire for those queries that can be satisfied by collecting answers directly from the applicant. The questionnaire can be filled out in paper or electronic form by the applicant or by a clerk assisting the applicant. The questionnaire displays generated applicant-specific queries that can be satisfied by collecting answers from the applicant. The data entered into the questionnaire is then stored as collected medical information corresponding to the displayed queries.

The data can be stored with the FIDs as described above and preferably be displayed to a physician for review or verification.

In certain embodiments, the clerk's data collection protocol displays generated applicant-specific queries that are to be collected from medical records. For each query, the protocol preferably displays an instruction to the clerk, for example, "Retrieve data from previous x-ray charts." The instructions may be retrieved from instructions stored in the knowledge library 118 that are associated with stored general medical information queries. In another embodiment, the system automatically notifies a custodian of medical records via email, voice mail or paper report to search for the medical information specified by the queries.

In yet another embodiment, the employment determination system 100 is connected to an electronic data storage that stores existing medical records as EMR, in, for example, the applicant database 160. The electronic data storage may comprise any type of computer-readable media, including hard disk drives, removable magnetic disks, removable optical disks, magnetic cassettes, flash memory cards, digital video disks, Bernoulli cartridges, random access memories, read-only memories, and the like. The employment determination system 100, via an electronic records querying module (not shown), may automatically search the data storage and collect required medical information from the EMR. If the applicant database 160 is encrypted, or if access to this database is otherwise restricted, the employment determination system 100 may be configured to store the requisite authentication in order to access the applicant database 160 freely. In another embodiment, the clerk or medical provider may be required to provide such authentication before the employment determination system 100 can access the applicant database 160.

The employment determination system 100 may communicate with the applicant database 160 by any of a variety of electronic communications methods well known to those of skill in the art, including over a local area network, a wide area network, the Internet (preferably by an encrypted connection), a phone line, combinations of the same and the like. As is well understood by those of skill in the art, the terms "over" and "through" in reference to network access are used synonymously; thus, one may access data over the Internet or through the Internet. In a preferred embodiment, the applicant database 160 advantageously stores medical information in a format that may easily be correlated to the medical information queries. For example, the applicant database 160 may be formatted to a particular standard that is widely adopted, and which facilitates access by other software applications that have also adopted the particular standard. However, in other embodiments, the employment determination system 100 may comprise sophisticated protocols for querying the applicant database 160 and for correlating the queries with meaningful information.

In order to improve efficiency, the employment determination system 100 may first search the electronic data storage for medical information that is responsive to the generated applicant-specific queries. In one embodiment, the employment determination system 100 may separate the exam queries from the medical record queries only after applicant-specific queries have been answered using the evidence in the EMR. In another embodiment, as illustrated, the protocols may be created before the applicant database 160 is interrogated. In another embodiment, the employment determination system 100 may substantially simultaneously search the electronic data storage and also provide a clerk's protocol according to which the applicant-specific queries may be answered from older, paper-based medical records.

Follow-Up Queries Based on Collected Medical Information

In certain embodiments, the query creation module 122 may create conditional applicant-specific queries. For example, if a required exam reveals an abnormal condition, then additional medical information may be required according to the rules collection module 112 or according to medical knowledge module 114. Such additional medical information queries are called conditional queries. The query whose medical information may trigger the conditional queries is called a triggering query. In certain embodiments, a triggering query may be associated with one or more sets of conditional queries. For example, a positive result of a laboratory test for a triggering query may require a first set of conditional queries, and a negative result may require a second set of conditional queries.

In one embodiment, the FID of a triggering query stored in the knowledge library 118 includes a list of the FIDs of the conditional queries. In another embodiment, each query is stored as an object in the knowledge library 118, and a triggering query object includes pointers to point to its conditional query objects. In yet another embodiment, the FID of a triggering query includes a flag code to indicate it is a triggering query. In certain embodiments, a triggering query table includes a first field that stores the FID of a triggering query and a second field that stores the FIDs of the corresponding conditional queries. In each embodiment, the knowledge library 118 may also store a triggering rule that indicates under what conditions the conditional queries are needed, such as, for example, "when the triggering query returns a positive test result" or "when the triggering query's medical information is not available."

In certain embodiments, regardless of the storage embodiments, when the applicant-specific query creation module 122 generates a triggering query as an applicant-specific query, the conditional queries for the triggering query are preferably also generated as applicant-specific queries. The protocol creation modules 134 and 136 may identify a triggering query and preferably display its corresponding conditional queries following the triggering query. The medical provider's exam protocol, clerk's data collection protocol and applicant's questionnaire preferably include instructions to explain the triggering rules, such as, for example, "If this test result is positive, then answer the following questions."

The conditional queries may be displayed after the medical information for the triggering query is collected. For example, a medical provider's exam protocol is displayed to the medical provider on the screen of an electronic device, and the medical provider enters collected medical information into the electronic device. As the medical provider enters the medical information for a triggering query into the electronic device, the employment determination system 100 compares the entered medical information with the triggering query's triggering rule stored in the knowledge library 118 and displays the conditional queries according to the triggering rule. If the conditional queries are to be collected from physical exams, they may be displayed on the electronic device or on an additional paper report. The conditional queries can also be displayed on an applicant questionnaire or clerk's data collection protocol in electronic or paper form.

Creating Medical Report

Referring back to FIG. 1, after medical information is collected from physical examinations, laboratory tests, medical records and/or the applicant questionnaire, the collected medical information is used by a medical report creation module 142 to create a medical report. In certain embodiments, the medical report includes collected medical information, for example medical history data and other data, in a narrative form.

For example, for an employment screening procedure to work in a particular environment, the medical report may display a summary of applicant-specific queries and medical information and corresponding medical requirements. In one preferred embodiment described above, the FID for each query includes a category code, a requirements code and a data query code. The requirements may thus be displayed along with the collected medical information of the query. In such embodiments, the report displays relationships of medical conditions, medical information and requirements.

The medical report can be used by medical providers to review the applicant's medical information and to familiarize the medical providers with the associated employment requirements. The medical report can also be used by program administrative personnel to review the applicant's medical information relating to the potential employment determination. In some embodiments, medical reports can be used interchangeably with employment assessments, which are described below.

Depending on the employer, reports of different formats can be generated to conform to a commonly accepted format. For example, the medical information queries can be grouped by body system for a first employer and grouped by class on another report for a second employer.

Creating Employment Assessment

Referring back to FIG. 1, the employment assessment creation module 152 creates an employment assessment to assist program administrative personnel to adjudicate the employment requests of an applicant.

In certain embodiments, the employment assessment creation module 152 also recommends an employment determination. For example, the employment determination can be generated based on a set of mathematical formulas, a rule-based system, an expert system, a self-learning neural network, a fuzzy logic system, combinations of the same and the like. The recommended employment determination may include a numerical value representing the suitability of the candidate, a numerical value representing the dollar amount necessary to insure a potential employee, a binary value representing a decision to grant or deny the employment application, combinations of the same and the like. The program administrative personnel can review the employment assessment and accept, reject or modify the recommended employment determination.

In certain embodiments, the components of the employment determination system 100 are modules that comprise logic embodied in hardware or firmware or may be implemented in collection of software instructions written in a variety of computer languages, commercial applications and operating platforms. For example, the employment determination system 100 may be implemented in whole or in part in Visual Basis, C, SQL, and so forth. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors.

With reference to the flowcharts described above, it will be understood that each block of the flowchart illustrations can be implemented by computer program instructions. These computer program instructions may be provided to a processor of a general purpose computer, special purpose computer, or other programmable data processing apparatus, such that the instructions, which execute via the processor of the computer or other programmable data processing apparatus, create means for implementing the acts specified in the flowchart.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the acts specified in the flowchart.

Certain aspects, advantages and novel features of the invention have been described herein. Of course, it is to be understood that not necessarily all such aspects, advantages or features will be embodied in any particular embodiment of the invention. The embodiments discussed herein are provided as examples of the invention, and are subject to additions, alterations and adjustments. Therefore, the scope of the disclosure should be defined by the following claims.

What is claimed is:

1. An automated system for processing medical information for an employment determination, the automated system comprising:
   a data storage configured to store general medical information queries associated with an employment rules collection;
   a query generation module configured to receive screening procedure data concerning an applicant, and to select a plurality of selected medical information queries specific to the applicant from a subset of the general medical information queries, the subset comprising queries that vary by applicant; and
   an employment assessment module configured to provide an employment assessment based on answers to the selected medical information queries;
   wherein the query generation module is configured to generate the plurality of selected medical information queries prior to receiving responses by the applicant to the subset of general medical information queries.

2. The automated system of claim 1, wherein the selection of the plurality of selected medical information queries is based at least in part on, and limited by, the screening procedure data and the employment rules collection.

3. The automated system of claim 1, wherein the screening procedure data further concerns an employer and an occupation, and the plurality of selected medical information queries are specific to the employer and the occupation.

4. The automated system of claim 3, wherein the selected medical information queries vary by applicant, vary by employer, and vary by occupation.

5. The automated system of claim 1, wherein the employment assessment comprising a recommended employment determination.

6. The automated system of claim 1, further comprising a report creation module configured to output data indicative of a medical report based at least on medical information obtained based on answers to the selected medical information queries.

7. The automated system of claim 6, wherein the medical report includes a summary of queries specific to the applicant, and medical information and corresponding medical requirements.

8. The automated system of claim 1, wherein the plurality of selected medical information queries includes a first set of exam queries and a second set of medical record queries.

9. The automated system of claim 1, further comprising a database configured to store information from electronic medical records (EMR) associated with the applicant.

10. The automated system of claim 1, further comprising a rules collection module configured to store the employment rules collection.

11. A method for assisting medical information collection for an employment determination of an applicant, the method comprising:
- identifying a screening procedure for assisting in an employment determination, wherein the screening procedure is correlated, by a computer, with an employment event concerning an individual;
- generating a plurality of selected medical information queries specific to the individual, based at least in part on, and limited by, the screening procedure and an employment rules collection, the plurality of selected medical information queries comprising queries that vary by individual; and
- generating an employment assessment based on received medical information data indicative of respective responses to the plurality of selected medical information queries;
- wherein the plurality of selected medical information queries specific to the individual is generated prior to receiving responses by the individual.

12. The method of claim 11, wherein the employment event further concerns an employer and an occupation, and wherein the plurality of selected medical information queries are specific to the employer and the occupation.

13. The method of claim 12, wherein the selected medical information queries vary by individual, vary by employer, and vary by occupation.

14. The method of claim 11, wherein the employment assessment comprises a recommended employment determination.

15. The method of claim 14, additionally comprising displaying the recommended employment determination.

16. The method of claim 11, additionally comprising eliminating duplicate generated medical information queries.

17. The method of claim 11, wherein at least a portion of the medical information data is received from an electronic computer-readable data storage.

18. The method of claim 11, wherein receiving the medical information data further comprises receiving medical information collected by a medical provider.

19. The method of claim 18, wherein receiving the medical information collected by the medical provider further comprises reviewing and extracting data from medical records.

20. The method of claim 18, wherein receiving the medical information collected by the medical provider further comprises receiving a medical history of the individual.

21. The method of claim 20, wherein the medical history comprises at least one of a family history and a social history.

22. The method of claim 18, wherein receiving the medical information collected by the medical provider further comprises receiving data from a physical exam.

23. The method of claim 11, additionally comprising displaying at least a portion of the generated medical information queries in a medical provider's exam protocol.

24. The method of claim 11, additionally comprising displaying at least a portion of the generated medical information queries in an assistant's data collection protocol.

25. The method of claim 11, additionally comprising displaying at least a portion of the generated medical information queries in an applicant questionnaire.

26. A non-transitory machine-readable medium having machine-readable instructions for performing a method of:
- identifying a screening procedure for assisting in an employment determination, wherein the screening procedure is correlated, by a computer, with an employment event concerning an individual;
- generating a plurality of selected medical information queries specific to the individual, based at least in part on, and limited by, the screening procedure and an employment rules collection, the plurality of selected medical information queries comprising queries that vary by individual; and
- generating an employment assessment based on received medical information data indicative of respective responses to the plurality of selected medical information queries;
- wherein the plurality of selected medical information queries specific to the individual is generated prior to receiving responses by the individual.

* * * * *